United States Patent

Wand et al.

[11] Patent Number: 5,167,855
[45] Date of Patent: Dec. 1, 1992

[54] FERROELECTRIC LIQUID CRYSTAL COMPOSITIONS CHIRAL HALOALKOXY TAIL UNITS

[75] Inventors: Michael Wand; Rohini Vohra; David Walba, all of Boulder, Colo.

[73] Assignee: University Research Corporation, Boulder, Colo.

[21] Appl. No.: 556,360

[22] Filed: Jul. 20, 1990

Related U.S. Application Data

[63] Continuation-in-part of Ser. No. 164,233, Mar. 4, 1988, Pat. No. 5,051,506.

[51] Int. Cl.$^5$ ............... C09K 19/52; C09K 19/12; C07D 21/72; C07D 239/02
[52] U.S. Cl. ............... 252/299.01; 252/299.66; 252/299.67; 252/299.61; 544/298; 546/346
[58] Field of Search ............... 252/299.61, 299.01, 252/299.66, 299.67; 544/298; 546/346

[56] References Cited

U.S. PATENT DOCUMENTS

| | | | |
|---|---|---|---|
| 4,556,727 | 12/1985 | Walba et al. | 560/73 |
| 4,695,650 | 9/1987 | Walba et al. | 560/109 |
| 4,695,651 | 9/1987 | Higuchi et al. | 560/141 |
| 4,725,688 | 2/1988 | Taguchi et al. | 544/298 |
| 4,728,458 | 3/1988 | Higuchi et al. | 252/299.65 |
| 4,732,699 | 3/1988 | Higuchi | 252/299.66 |
| 4,770,503 | 4/1988 | Buchecker et al. | 350/350 R |
| 4,777,280 | 10/1988 | Eidman et al. | 558/389 |
| 4,795,587 | 1/1989 | Ohno et al. | 252/299.61 |
| 4,798,680 | 1/1989 | Nohira et al. | 252/299.01 |
| 4,886,623 | 12/1989 | Mitsuhashi | 252/299.65 |
| 4,917,821 | 4/1990 | Mori et al. | 252/299.63 |
| 4,954,600 | 9/1990 | Hachiya et al. | 528/89 |
| 4,973,426 | 11/1990 | Ohno et al. | 252/299.66 |

FOREIGN PATENT DOCUMENTS

| | | |
|---|---|---|
| 0220747 | 5/1987 | European Pat. Off. |
| 0225236 | 2/1988 | European Pat. Off. |
| 0263437 | 4/1988 | European Pat. Off. |
| 0267585 | 5/1988 | European Pat. Off. |
| 0269062 | 6/1988 | European Pat. Off. |
| 0278665 | 8/1988 | European Pat. Off. |
| 62-111939 | 5/1987 | Japan. |
| 62-258361 | 11/1987 | Japan. |
| 63-264573 | 11/1988 | Japan. |
| 8606373 | 11/1986 | PCT Int'l Appl. |
| 8902425 | 3/1989 | PCT Int'l Appl. |
| 8705018 | 8/1987 | World Int. Prop. O. |

OTHER PUBLICATIONS

Furukawa et al. (1988) Ferroelectrics 85:451–459.
Chemical Abstract No. 109:201686w (p. 795).

Primary Examiner—Robert L. Stoll
Assistant Examiner—C. Harris
Attorney, Agent, or Firm—Greenlee & Winner

[57] ABSTRACT

The subject application discloses chiral nonracemic compositions of the general formula:

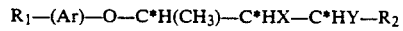

$R_1-(Ar)-O-C^*H(CH_3)-C^*HX-C^*HY-R_2$ wherein: $R_1$ is an achiral tail of two to sixteen carbons; Ar is an achiral FLC core of at least two rings; * denotes a chiral or potentially chiral carbon; X is a halide and Y is H or a halide; $R_2$ comprises the distal segment of the chiral tail and has one to ten carbon atoms; the $-O-C^*H(CH_3)-C^*HY-C^*HY-CH_2-O-$ segment comprises the chiral proximal segment of the chiral tail, and the proximal segment is selected from the diastereomers and enantiomers:

1S-methyl-2S-halo
1S-methyl-2R-halo
1R-methyl-2R,3R-dihalo
1R-methyl-2R,3S-dihalo
1R-methyl-2S,3S-dihalo
1R-methyl-2S,3R-dihalo
1R-methyl-2R-halo
1R-methyl-2S-halo
1S-methyl-2S,3S-dihalo
1S-methyl-2S,3R-dihalo
1S-methyl-2R,3R-dihalo
1S-methyl-2R,3S-dihalo.

15 Claims, No Drawings

FERROELECTRIC LIQUID CRYSTAL COMPOSITIONS CHIRAL HALOALKOXY TAIL UNITS

This invention was made with partial support of the United States Government under National Science Foundation Grant no. ISI8860992. The United States Government has certain rights in this invention.

RELATEDNESS OF THE APPLICATION

This application is a continuation-in-part of copending, U.S. Ser. No. 164,233, filed Mar. 4, 1988, which is incorporated herein in its entirety by reference.

FIELD OF THE INVENTION

The present invention relates to ferroelectric liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. Since the coupling to an applied electric field by this mechanism is rather weak, the resultant electro-optical response time may be too slow for many potential applications.

Liquid crystal displays have a number of unique characteristics, including low voltage and low power of operation, which makes them perhaps the most promising of the non-emissive electro-optical display candidates available with today's technology. However, slow response and insufficient nonlinearity can impose limitations for many potential applications. The requirement for speed may become especially important in proportion to the number of elements which have to be addressed in a device. This may result in increasingly impractical production costs for the potential use of such devices in flat-panel displays for use in video terminals, oscilloscopes, radar and television screens.

It has been shown by N. A. Clark and S. T. Lagerwall in Appl. Phys. Lett. 36:899 (1980) and in U.S. Pat. No. 4,367,924 that electro-optic effects with sub-microsecond switching speeds are achievable using the technology of ferroelectric liquid crystals (FLCs). Some display structures prepared using FLC materials, in addition to the high speed (about 1,000 times faster than currently used twisted nematic devices) reported by these investigators, also exhibit bistable, threshold sensitive switching, making them potential candidates for light modulation devices including matrix addressed light valves containing a large number of elements for passive displays of graphic and pictorial information, as well as for optical processing applications. A recent review of the applications of FLC devices is given by Lagerwall, S. T. and Clarke, N. A. (1989) Ferroelectrics 94:3-62.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the molecules in the ferroelectric liquid crystal phase with the applied field. When the sign of the applied field is reversed, realignment or switching of the FLC molecules occurs. This switching can be employed for light modulation Within a large range of electric field strengths, the switching speed (optical rise time) is inversely proportional to applied field strength and polarization or dipole density (P), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture. The components of FLC mixtures can also be adjusted to vary phase transition temperatures or to introduce desired LC phases. Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains a 2-methylbutyl chiral tail. Pure DOBAMBC exhibits a smectic C* phase with a ferroelectric polarization of $-3$ nC/cm$^2$.

There are a number of reports of compounds containing phenylbenzoate, diphenyl, phenylpyrimidine and related cores coupled to chiral tail units which possess monotropic smectic C* phases displaying fast switching speeds at room temperature, or which can be employed as FLC dopants to induce high polarization and fast switching speeds when combined in mixtures with FLC host materials.

The following are exemplary reports of such FLC compounds:

Walba et al., U.S. Pat. No. 4,556,727 reports phenylbenzoates having non-racemic 2-alkoxy-1-propoxy tails. Eidman and Walba, U.S. Pat. No. 4,777,280 report chiral 1-cyanoalkoxy phenylbenzoates. Walba and Razavi, U.S. Patent 4,695,650 report chirally asymmetric reverse ester phenylbenzoates having chiral 1-haloalkyl tail units.

Ohno et al. (1989) U.S. Pat. No. 4,795,587 refers to liquid crystal compounds exhibiting smectic C phases which contain a phenylpyridine core having the formula:

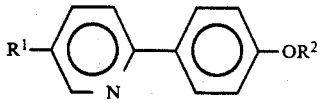

where $R^1$ is an alkyl group having seven to twelve carbon atoms and $R^2$ is an alkyl group having five to twelve carbon atoms.

Japanese patent documents JP 63264573 and JP 62258361 refer to optically active 6-substituted-pyridine-3-carboxylic acid esters useful as ferroelectric smectic liquid crystals. Optically active 6-substituted-pyridine-3-carboxylicacidesters obtained from reaction of dodecyloxybenzoic acid, thionyl chloride and 6-hydroxynicotinic acid (S)-2-methylbutyl ester are specifically referred to. Japanese patent document JP 62175465 refers to ester compounds contained in liquid crystal compositions exhibiting nematic phases. 2-(trans-4-ethyl-cyclohexyl)- 5-nicotinic acid3-fluoro-4-cyanophenyl ester is referred to specifically.

Walba et al. (1986) J. Amer. Chem. Soc. 108:7424–7425 and Walba and Vohra, U.S. Pat. No. 4,648,073 and U.S. Pat. No. 4,705,874 disclose ferroelectric (chiral) smectic liquid crystal compounds having an achiral core and chiral tail units derived from (2,3)-alkyloxiranemethanols which possess a high ferroelectric polarization density. The ferroelectric liquid crystal materials reported have the following general formulas:

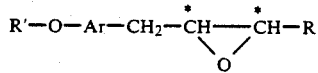

where R is an alkyl of one to seven carbon atoms and R' is an alkyl of five to twelve carbon atoms and Ar is phenylbenzoate or biphenyl.

Hemmerling et al. (1988) European Patent Application, Pub. No. 263437 refers to chiral aryl-2,3-epoxyalkylethers FLC compounds having phenylpyrimidine or phenylpyridazine cores of the formula:

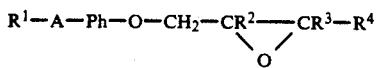

where A is a diazine-2,5,-diyl or diazine-3,6-diyl, $R^1$ is a straight chain or branched alkyl group having 1-12 carbon atoms wherein one or two non-neighboring $CH_2$ groups is replaced with an O or S atom, $R^{2-4}$ are, independent of one another, H, a straight chain alkyl group having 1-12 carbon atoms or a branched alkyl group having 3-10 carbon atoms wherein $R^1$, $R^2$ and $R^3$ are not all H. Compounds in which $R^2$ and $R^3$ are both H having extrapolated polarization densities ($P_{ext}$) in the range from 30-70 nC/cm₂ are reported.

Walba and Razavi, U.S. Pat. No. 4,835,295, discloses chirally asymmetric phenyl and biphenylbenzoates having chiral 2,3-epoxy alkyl or 1-halo-2,3-epoxy alkyl tails which are useful as components of FLC materials. The compounds disclosed have the formula:

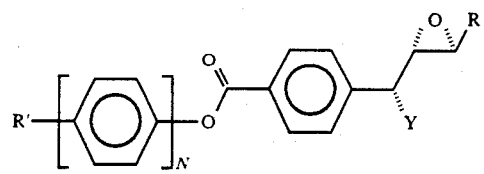

where R' is an alkyl or alkoxyl group having three to fifteen carbon atoms, R is an alkyl group having three to fifteen carbon atoms, n=1 or 2, and Y is a halogen or hydrogen. It is also disclosed, therein, that 1-haloepoxides of formula A can impart higher polarization densities and higher switching speeds in FLC mixtures than their diastereomers of formula B. It is suggested that the difference in properties of A and B is due to the relative alignment of the epoxide and halogen bond dipoles in the isomer.

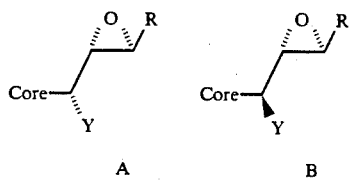

Furukawa, K. et al. (1988) Ferroelectrics 85:451–459 refers to chiral smectic C compounds having an ester group in the core and an optically active tail group, either alkoxy or alkoxy carbonyl, with an electronegative substituent, either a halogen or cyano group, ortho to the chiral tail, for example:

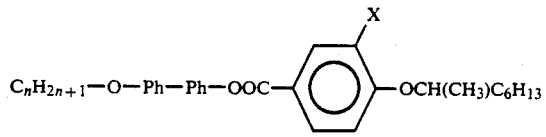

where X=H, Halogen or CN.

While a number of useful ferroelectric liquid crystal materials (both pure compounds and mixtures) have been reported, there is a growing need for FLC materials with varying properties of temperature range, tilt angle and switching speed for use in varied applications. Further, there is a need for FLC dopants with varying mixing properties (which are dependent, at least in part, on chemical composition) for use in the preparation of FLC mixtures. FLC dopants which impart high polarization density to, and retain low viscosity in, such mixtures are of particular interest.

SUMMARY OF THE INVENTION

The present invention provides a class of chirally asymmetric molecules which are useful as components of ferroelectric liquid crystal materials. These compounds can impart the properties of high ferroelectric polarization density and fast electro-optical switching speeds on low polarization materials when mixed with such materials to form ferroelectric liquid crystal compositions. Alternatively, certain of the compounds of the present invention in pure form can also possess stable smectic C* phases having high polarization density.

The composition of the subject invention comprises chiral nonracemic compositions of the general formula:

wherein: $R_1$ is an achiral tail of two to sixteen carbons; Ar is an achiral FLC core of at least two rings; * denotes a chiral or potentially chiral carbon; X is a halide and Y is H or a halide; $R_2$ comprises the distal segment of the chiral tail and has one to ten carbon atoms; the —O—C*H(CH$_3$)—C*HX—C*HY—CH$_2$— segment comprises the chiral proximal segment of the chiral tail, and the proximal segment is selected from the diastereomers and enantiomers:

| | |
|---|---|
| 1S-methyl-2S-halo | 1R-methyl-2R-halo |
| 1S-methyl-2R-halo | 1R-methyl-2S-halo |
| 1R-methyl-2R,3R-dihalo | 1S-methyl-2S,3S-dihalo |
| 1R-methyl-2R,3S-dihalo | 1S-methyl-2S,3R-dihalo |
| 1R-methyl-2S,3S-dihalo | 1S-methyl-2R,3R-dihalo |
| 1R-methyl-2S,3R-dihalo | 1S-methyl-2R,3S-dihalo. |

The preferred proximal segments are:

| | |
|---|---|
| 1S-methyl-2S-halo | 1R-methyl-2R-halo |
| 1S-methyl-2R,3R-dihalo | 1R-methyl-2S,3S-dihalo |

The achiral cores are rigid, linear moieties. Preferred cores are those that are chemically stable and which do not impart high orientational viscosity in the liquid crystal phase. In the present invention, cores containing at least two aromatic rings are preferred such as those cores based on phenylbenzoates, phenylpyridines, phenylpyrimidines, biphenyls, terphenyls, biphenyl pyridines, biphenylpyrimidines and biphenylbenzoates wherein achiral and chiral tails are located on non-central or outside aromatic rings and are para with respect to the bond of their aromatic ring to the adjacent ring or to carbon or oxygen atoms bridging to the adjacent ring. Examples of some of the ferroelectric (FLC) cores useful in the subject invention are illustrated in Table 1.

As used herein "phenylbenzoate" includes forward and reverse phenylbenzoates:

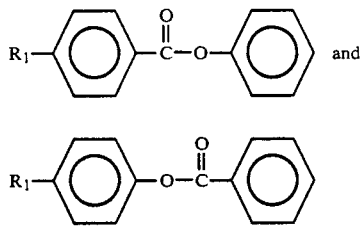 and

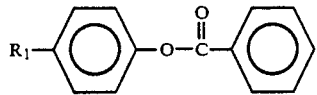

"Phenylpyrimidine" means 2,5-substituted and 3,6-substituted phenylpyrimidines. Additionally, "phenylpyridine" means 2,5-substituted phenylpridines.

The chiral tail is positioned at the para position on its aromatic ring relative to the bond of its ring to the adjacent ring or to the carbon or oxygen atoms bridging its ring to the adjacent ring. Likewise, the achiral tail is positioned at the para position on its aromatic ring relative to the bond of its ring to the adjacent ring or to carbon or oxygen atoms bridging its ring to the adjacent ring. For example, in a biphenyl core, the chiral and achiral tails are positioned 4,4'.

Examples of some of the cores useful in the subject invention are illustrated in Table 1. In Table 1, $R_1$ indicates the achiral tail and R* indicates the chiral tail, including the proximal and distal ($R_2$) segments.

The achiral tail, $R_1$, can be an alkyl, alkenyl or alkoxy group. $R_1$ can contain two to sixteen carbon atoms; it preferably contains five to sixteen carbons; and it most preferably contains eight carbons. $R_1$ can be straight chain or branched. Branching can broaden the smectic C phase of the compound itself or of an FLC mixture containing the compound. The branching effect is enhanced when branching is more distant from the core. It has also been observed that if branching occurs at carbons 2-8 (relative to the core), the polarization density of the FLC molecule is generally not affected.

TABLE 1

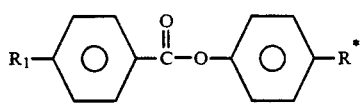
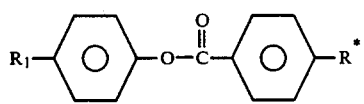
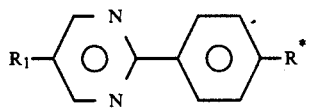
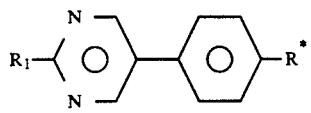
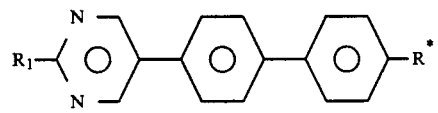
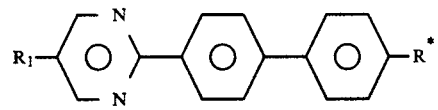
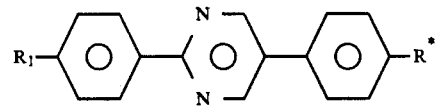
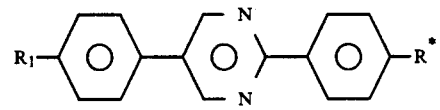
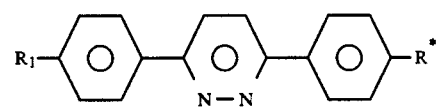

TABLE 1-continued

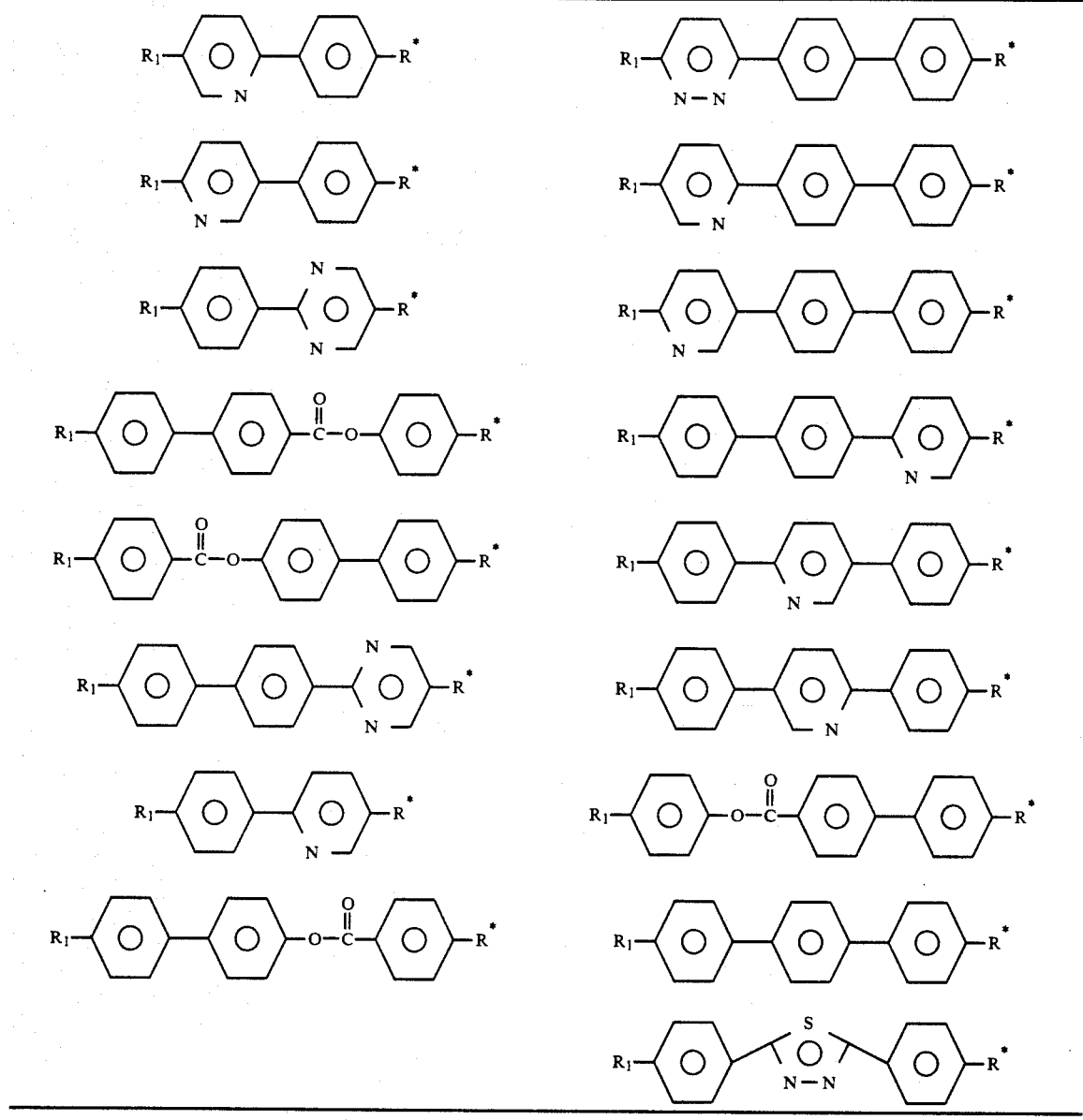

As described in PCT/EP88/00724 (WO 02425, p.13), oxygen or sulfur atoms can replace non-adjacent $CH_2$ groups in the achiral tail to produce, for example, alkoxy or thiaalkyl tails. It has been observed that such substitutions do not significantly impair the polarization density; such substitutions can impart a broader smectic C* phase of the compound itself or of an FLC mixture containing the compound.

When $R_1$ is an alkenyl, the double bonds can be located at any position in $R_1$'s chain, including the omega position. Positioning of a double bond in the omega position creates a precurser to an FLC polymer. For example, an FLC compound of the subject invention containing omega-alkenyl achiral tails could be reacted with polysiloxane to form a polymeric FLC.

When $R_1$ is an alkenyl, the double bonds can be cis or trans. However, trans bonds are preferred because cis is likely to result in reduced solubility of the dopant FLC in the host material. Additionally, cis bonds can narrow the smectic C* range.

The halides of the chiral proximal segment are preferably fluorine and chlorine. X and Y can be the same or different halides.

It has been observed that FLC dopants comprising one enantiomer of an enantiomer pair, such as:

| Enantiomer Pairs | | |
|---|---|---|
| 1S-methyl-2S-halo | and | 1R-methyl-2R-halo |
| 1S-methyl-2R-halo | and | 1R-methyl-3S-halo |
| 1R-methyl-2R,3R-dihalo | and | 1S-methyl-2S,3S-dihalo |
| 1R-methyl-2R,3S-dihalo | and | 1S-methyl-2S,3R-dihalo |
| 1R-methyl-2S,3S-dihalo | and | 1S-methyl-2R,3R-dihalo |
| 1R-methyl-2S,3R-dihalo | and | 1S-methyl-2R,3S-dihalo | function equivalently in FLC host materials as the FLC dopant comprising the other enantiomer of the enantiomer pair, except that the sign of their polarization densities is reversed. As will be understood by those in the art, the sign of the polarization of an FLC dopant should be the same as that of the host material in order to achieve high polarization mixtures. It is a feature of this invention that either enantiomer of the above-identified enantiomer pairs can be prepared. This allows choice of the appropriate enantiomers for use with a particular host material.

The distal segment ($R_2$) of the chiral tail of the composition of the subject invention can be an alkyl or alkenyl group of one to ten carbons. As the size of the distal segment increases, it can increase the viscosity of the FLC compound; for this reason, it is preferred that $R_2$ contain two to three carbons.

$R_2$ can be straight chain or branched. Branching can broaden the smectic C* phase; generally, this effect is enhanced when branching is more distant from the core.

If $R_2$ is an alkenyl, the double bonds can be located at any position in the segment. If $R_2$ contains double bonds, they may be cis or trans. However, trans bonds are preferred because cis is likely to result in reduced solubility of the dopant FLC in the host material. Additionally, cis bonds will likely narrow the smectic C* range.

$R_2$ can contain chiral carbons. Chirality in the distal segment, like that in the proximal segment, contributes to polarization density of the FLC molecule. The distal segment chirality can enhance or reduce the polarization density of the FLC molecule as imparted by the proximal segment. The closer the chiral groups in the distal segment to the proximal segment, the greater the impact of the $R_2$ chirality on the dipole created by the proximal segment. Whether a particular chiral $R_2$ enhances or decreases polarization density can be determined by routine testing by known methods of FLC compounds containing the chiral $R_2$ in question. Synthesis methods of $R_2$-containing FLC compounds of the subject invention are described hereinbelow and/or are known to those of skill in the art. Methods for measuring polarization density are also described hereinbelow.

DETAILED DESCRIPTION OF THE INVENTION

The compositions of the subject invention are synthesized by several methods, described hereinbelow, from a 4',4-substituted $R_1$—(Ar)—OH compound. The 4',4-substituted $R_1$—(Ar)—OH compounds are either commercially available or can be synthesized by known methods from readily available starting materials. For example, the synthesis of 4'-decyloxyphenyl-4-hydroxybenzoate (X, where $R_1$=decyloxy) is described in the Examples.

In the Examples, the Ar employed is phenylbenzoate; however, as discussed hereinabove, any suitable FLC core can be used in place of phenylbenzoate.

To synthesize 4'-$R_1$-phenyl-4-[(1-methyl-2-halo)alkoxy]benzoates, 4'-$R_1$-phenyl-4-hydroxybenzoate (X) is coupled to a chiral 1-methyl-(2,3-epoxy)alkanol, the epoxy ring is opened, followed by stereospecific halogenation of the resulting hydroxy group. The procedure is illustrated by the synthesis of 4'-decyloxyphenyl-4[(1S,4-dimethyl-2S-fluoro)pentyloxy]benzoate (XVI, where $R^1$=decycloxy, X=F, and $R_2$=isopropyl) as described in Example 2a and as illustrated in Scheme 4.

To obtain the enantiomer of the 4'-$R_1$-phenyl-4-[(1-methyl-2-halo)alkoxy]benzoates produced by the method of Example 2a, the procedure of Example 2a is followed with the exception that (1S,4-dimethyl-2R,3R-epoxy)pentanol, the enantiomer of (1R,4-dimethyl-2S,3S-epoxy)pentanol (XIII, where $R_1$=isopropyl, used in Example 2a), is used in place of (1R,4-dimethyl-2S,3S-epoxy)pentanol.

The synthesis of diastereomers of 4'-$R_1$-phenyl-4-[(1-methyl-2-halo)alkoxy]benzoates produced by the method of Example 2a, can be accomplished by methods known to those of skill in the art, or as described hereinbelow. For example, the synthesis of 4'-decyloxyphenyl-4-[(1R, 4-dimethyl-2S-fluoro)pentyloxy]benzoate is accomplished by following the method of Example 2a with the exception that (1S-methyl-2S,3S-epoxy)pentanol (XI, where $R_2$=isopropyl) is used in place of its diastereomer, (1R-methyl-2S,3S-epoxy)pentanol (XIII, where $R_2$=isopropyl).

To synthesize 4'-$R_1$-phenyl-4-[(1-methyl-2,3-dihalo)alkoxy]benzoates, 4'-$R_1$-phenyl-4-hydroxybenzoate (X) is coupled to a chiral 1-methyl-2,3-epoxy alkanol, the epoxy ring is opened and treated with a halogenating agent. The synthesis of 4'-$R_1$-phenyl-4-[(1-methyl-2,3-dihalo)alkoxy]-benzoates is exemplified by the synthesis of 4'-decyloxyphenyl-4-[(1S,4-dimethyl-2R,3R-difluoro)pentanyloxy]benzoate (XIX, where $R_1$=decyloxy, X and Y=F and $R_2$=propyl) as described in Example 3a and illustrated in Scheme 5.

To synthesize the enantiomer of the 4'-$R_1$-phenyl-4-[(1-methyl-2,3-dihalo)alkoxy]-benzoate produced by the method of Example 3a, the method of Example 3a is followed with the exception that (1S,4-dimethyl-2R,3R-epoxy)pentanol, the enantiomer of (1R,4-dimethyl-2S,3S-epoxy)pentanol (XIII, where $R_2$=isopropyl), is used in place of (1R,4-dimethyl-2S,3S epoxy)pentanol.

The diastereomers of 4'-decyloxyphenyl-4-[(1S,4-dimethyl-2R,3R-difluoro)pentanyloxy]-benzoate can be synthesized by known methods from readily available starting materials. For example, 4'-decyloxyphenyl-4-[(1R,4-dimethyl-2R,3R-difluoro)pentanyloxy]-benzoate, is synthesized by following the method of Example 3a with the exception that (1S,4-dimethyl2S,3S-epoxy)-pentanol (XI, where $R_2$=isopropyl), a diastereomer of (1R,4-dimethyl-2S,3S epoxy)pentanol (XIII, where $R_2$= isopropyl), is used in place of (1R,4-dimethyl-2S,3S epoxy)pentanol.

As is understood by those of skill in the art, the agents used in the methods described herein for opening the epoxy ring and for halogenating the resulting hydroxy group can be replaced by alternate agents to produce compositions in which X and/or Y=chloride or other halides, or in which X is a different halide from Y. For example, opening the epoxy ring with HCl rather than (HF)$_x$-pyridine results in a chlorohydrin rather than a fluorohydrin; treating the resulting hydroxy group with a halogenating agent, DAST, produces a chlorofluoro alkoxy proximal segment. However, treating the hydroxy group with chlorinating agent produces a dichloro alkoxy proximal segment.

SCHEME 1:

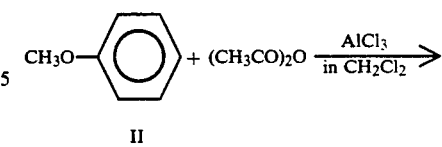

II

-continued
SCHEME 1:
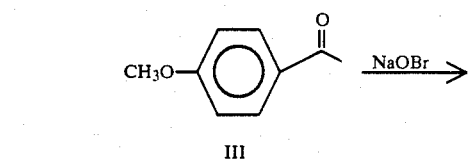
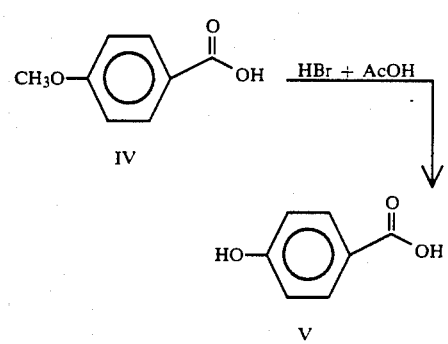
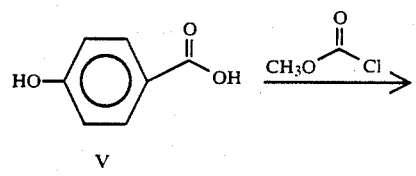
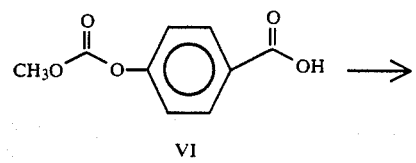
SCHEME 2:
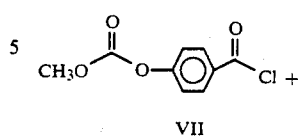
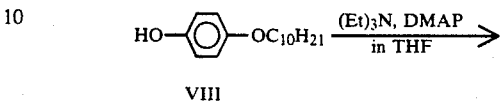
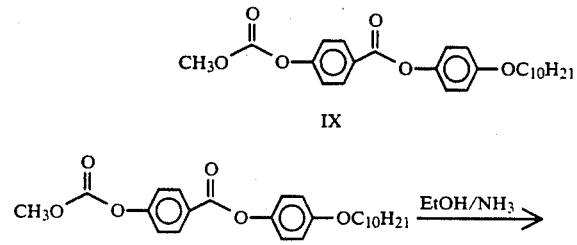
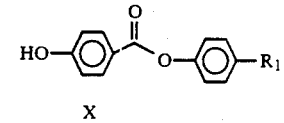
(R₁ = decyloxy)
SCHEME 3:
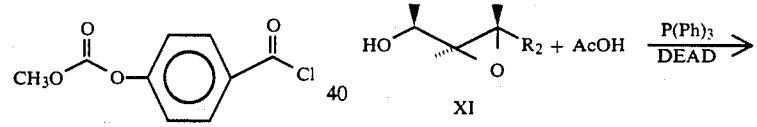
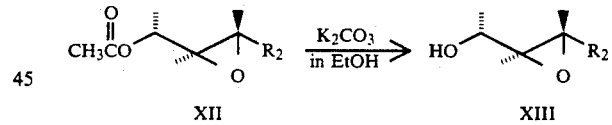
SCHEME 4:
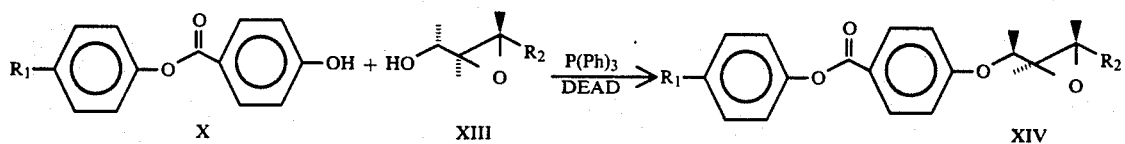
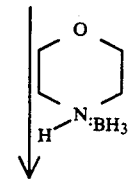

SCHEME 4:

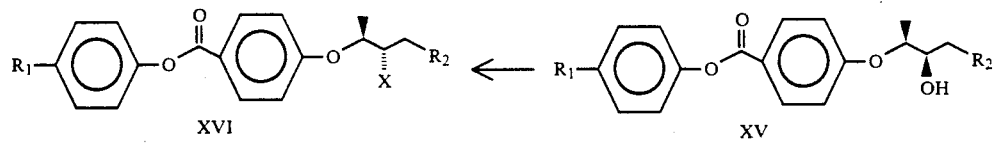

-continued

SCHEME 5:

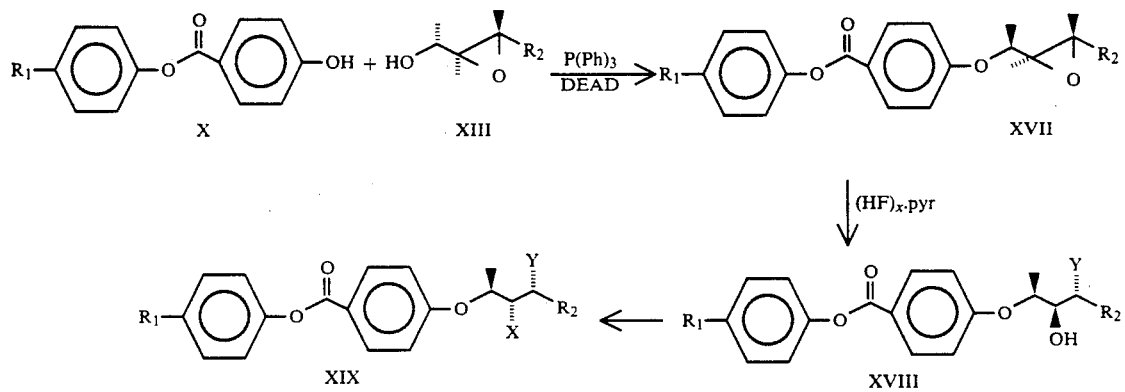

Many of the compounds of the subject invention, including compounds 4'-decyloxy-4-(1S,4-dimethyl-2S-fluoro)pentyloxybenzoate (general formula XVI) and 4'-decyloxy-4-(1S,4-dimethyl-2R,3R-difluoro)pentyloxybenzoate (general formula XIX) of Table 2, do not possess an enantiotropic or monotropic ferroelectric (smectic C*) liquid crystal phase. However, when these compounds are mixed with a known FLC host material, such as W82, mixtures are produced which possess ferroelectric smectic C* phases and improved polarization density relative to the host material alone. The polarization density of W82 is about $-1$ nC/cm$^2$. Because of their high polarization densities, the subject compositions can improve the polarization densities of FLC mixtures without significantly increasing the orientational viscosity of the mixture. The subject compositions can be used as compensating agents for the N* or C* helical pitch of an FLC composition.

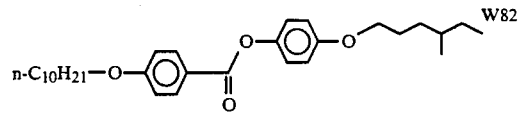

Table 2 summarizes the polarization density and phase sequence temperatures of 10% (w/w) mixtures of subject compositions with W82. In Table 2, the phases are noted as X=crystal, I=isotropic liquid, A=smectic A, C*=smectic C, F*=smectic F, and phase sequence temperatures are given in ° C. Spontaneous polarization densities ($P_s$) are given in nC/cm$^2$ and the magnitude of $P_s$ was measured by integration of the dynamic current response on reversing the applied electric field, as described in Martinot-Lagarde (1976) J. Phys. 37. C-3, p.129 and Martinot-Lagarde (1977) J. Phys. Lett. 38, L-17. $P_{s(ext)}$ is the polarization density for the subject composition as extrapolated from a 10% by weight mixture of the subject composition in W82.

Compositions of the subject invention can also-be mixed with host materials in any desired weight percentage. Generally, as the weight percentage of subject compositions in the host material is increased, the polarization density of the FLC mixture increases linearly. Depending on the intended application and desired polarization of the FLC mixture, a person of skill in the art can determine the appropriate concentration of subject compositions to incorporate in a host material to obtain the desired polarization. Because the polarization densities of the subject applications are high, low concentrations are typically used as dopants to obtain the desired polarization in the mixture. Generally, the concentrations of the dopants used in the host are less than about 20% (w/w). Such low concentrations avoid orientational viscosity that may be associated with the use of higher concentrations of such dopants.

Generally, as dopant concentration in an FLC mixture increases, the phase diagram of the mixture and the pitch may be altered. However, a person of skill in the art would be able to compensate for these effects.

Compositions of the subject invention can be mixed with any suitable host material. Suitable host materials vary with the intended application, but generally, solubility or miscibility with the dopant, broad C* phase temperature range (e.g., $-20°$ C. to $60°$ C.) and low orientational viscosity are considered desirable.

Additionally, the compounds of Table 2 can impart higher polarization densities in FLC mixtures than analogous compounds which do not have a halogenated chiral tail, such as 4'-decyloxyphenyl-4-(1-methylhexyloxy)benzoate. For example, a 10% by weight mixture of 4'-decyloxyphenyl-4-(1-methylhexyloxy)benzoate in W82 has an extrapolated polarization density of $-42$ nC/cm$^2$.

The improved polarization density of the compositions of the subject invention is believed to be due to the relative alignment of the dipole moments of oxygen and halide(s) bonds in the chiral tail. It should be noted that it is dipole orientation of the subject conformations in the oriented smectic C phase that affects polarization density. Only the components of the dipoles normal to the tilt plane effect polarization. The structure of the proximal and distal segments of the achiral tail and steric interaction between the groups will affect dipole orientation and the magnitude and sign of the polarization density. The relationship between dipole alignment and ferroelectric polarization density has been discussed for related molecules in Walba et al. (1986) J. Amer. Chem. Soc. 108:5210–5221 and Walba et al. (1986) J. Amer. Chem. Soc. 108:7424–7425, both of which are incorporated herein by reference.

As discussed hereinabove, subject compositions comprising the following proximal segments are preferred:

| | |
|---|---|
| 1S-methyl-2S-halo | 1R-methyl-2R-halo |
| 1S-methyl-2R,3R-dihalo | 1R-methyl-2S,3S-dihalo. |

Compositions comprising these proximal segments are preferred because they can have greater polarization densities relative to their diastereomers. It is believed that the improved polarization of the preferred compositions is due to the relative alignment of the dipoles of the proximal segment oxygen and halides with each other and substantially normal to the tilt plane of the FLC composition C* phase, as compared to compositions comprising the less preferred proximal segments.

Variation in the structure of the cores and length and degree of branching in the $R_1$ and $R_2$ groups of compounds of the subject invention can affect the liquid crystal properties of the pure material or mixtures containing them. For example, some of the compounds of the present invention may possess smectic C* phases while others do not and the characteristics of any such smectic C* phases (i.e., stability, temperature range) may vary. Furthermore, the switching speed is also affected by the orientational viscosity of the liquid crystal. The structure of the core as well as the size and branching of the $R_1$ and $R_2$ groups can affect viscosity. For example, it is expected that compounds of the present invention having phenylpyrimidine cores will show faster switching speeds than their phenylbenzoate and biphenyl analogues due to a lower orientational viscosity associated with the phenylpyridine core unit.

4'-decyloxyphenyl-4-hydroxybenzoate (X, where $R_1$=decyloxy) described hereinbelow and illustrated in Schemes 1 and 2.

Initially, anisole (II) was used to synthesize 4-methoxyacetophenone (III). $AlCl_3$ (0.6 mol) and acetic anhydride (0.4 mol) were placed in 250 ml of dry dicloromethane. The anisol (0.2 mol) was added dropwise over a period of 30 minutes to the reaction mixture which was then stirred with a magnetic stir bar for two hours. The reaction was judged complete by TLC. The reaction mixture was then poured in ice and stirred for one hour. The $CH_2Cl_2$ layer was separated and the water layer was extracted twice with $CH_2Cl_2$. Organic layers were combined and washed with 3N HCl and water, dried with anhydrous $MgSO_4$ and passed through a thick pad of silica. The solvent was rotary evaporated to obtain the crude product, which was crystallized from 7% (v/v) ethyl acetate in hexanes to obtain 70% yield of the crystallized product, 4-methoxyacetophenone (III).

4-methoxyacetophenone (11.5 g) was dissolved in 100 ml dioxane and freshly prepared NaOBr solution (as prepared below) was added dropwise, with constant stirring with a stir bar at room temperature. The NaOBr solution was prepared by dissolving 40 g of NaOH in 500 ml of water, cooling to 0° C. in an ice bath, and adding bromine (12.5 ml) dropwise while stirring with stir bar; bromine was added slowly so that the reaction mixture did not exceed 5° C. After overnight stirring of the 4-methoxyacetophenone, dioxane and NaOBr solution, the reaction mixture was diluted with water (200 ml). Since the reaction mixture was basic, the product, benzoic acid, was in water as its sodium salt. The resultant mixture was partitioned between ether and water. The ether layer was washed with dilute aqueous NaOH to extract any remaining product as Na salt. The aqueous layers were combined and acidified to pH 1 to precipitate the benzoic acid. The resulting acid was extracted with ether. The ether layer was washed with water a few times, dried with anhydrous $MgSO_4$, and filtered. Rotary evaporation of the ether fraction afforded 4-methoxybenzoic acid (IV) in 85% yield.

Next, the 4-methoxybenzoic acid (IV) was digested with HBr (20 ml) and glacial acetic acid (40 ml) overnight. Most of the acetic acid was distilled off and the

TABLE 2

Phase sequence, polarization and tilt angle data for C* mixtures using W82 as host and containing 10% (w/w) of the subject compositions.

| | Phase Sequence °C. | Tilt Ps | θ | Ps(ext) | Ps(ext) ÷ sin θ |
|---|---|---|---|---|---|
| MDW 215 (XVI) 4'-decyloxyphenyl-4-(1S,4-dimethyl-2S-fluoro) pentyloxybenzoate | I $\xrightarrow{64.6}$ A $\xrightarrow{75.3}$ C* $\longrightarrow$ X | −8.39 | 25 | −75 | −177 |
| MDW 194 (XIX) 4'-decyloxyphenyl-4-(1S,4-dimethyl-2R,3R-difluoro) pentyloxybenzoate | I $\xrightarrow{65.9}$ A $\xrightarrow{57.4}$ C* $\xrightarrow{18.3}$ F* $\xrightarrow{-2}$ X | −2.20 | 29.5 | −13 | −26 |

EXAMPLES

Example 1 Synthesis of 4'-$R_1$-phenyl-4-hydroxybenzoates (X)

This example illustrates the synthesis of 4'-$R_1$-phenyl-4-hydroxybenzoates, which can be used in the methods of the remaining Examples to produce the compositions of the subject invention. The synthesis of 4'-$R_1$-phenyl-4-hydroxybenzoates is illustrated by the synthesis of remaining mixture was diluted with water. The precipitated benzoic acid was extracted in ether; the ether layer was dried with anhydrous $MgSO_4$, filtered and rotary evaporated to produce 11.0 g of the 4-hydroxybenzoic acid (V).

4-methoxycarbonyloxy benzoic acid (VI) was synthesized as follows. 300 mmol of NaOH and 100 mmol of 4-hydroxybenzoic acid (V) were dissolved in 300 ml of water and cooled to −20° C. Methylchloroformate (150 mmol) was added dropwise to it. The slurry was stirred for four hours at −5° C. with a magnetic stir bar and left overnight in refrigerator. It was then acidified to pH 5 to precipitate the protected benzoic acid (VI). The precipitate was filtered and crystallized from acetonitrile to afford the clean product in 86% yield.

10 mmol of the protected benzoic acid (VI) was refluxed over night in neat oxalylchloride. Excess oxalylchloride was removed under vacuum and traces of it were removed under high vacuum. The resulting benzoyl chloride (VII) and 4-n-decyloxyphenol (VIII) (10 mmol) were dissolved in dry cold (0° C.) THF. Triethylamine (30 mmol) was added dropwise, followed by a catalytic amount of DMAP. The reaction mixture was stirred with a magnetic stir bar for three hours at room temperature. The solvent was then rotary evaporated and the residue was passed through a thick pad of silica using 20% (v/v) hexanes in $CH_2Cl_2$. The solvent was taken off under vacuum to obtain the product, 4'-decyloxyphenyl-4-methoxoxycarbonyloxybenzoate (IX), in 81.4% yield.

7 mmol of the 4'-decyloxyphenyl-4-methoxycarbonyloxy benzoate was dissolved in 100 ml of ethanol and 4 ml of 30% (v/v) $NH_3$ was added to it. The reaction mixture was stirred with a stir bar for half an hour. After the reaction was complete the solution was poured into water and cooled in dry ice. The precipitated product was filtered and recrystallized from acetonitrile to afford 4'-decyloxyphenyl-4-hydroxybenzoate (X) in 89% yield.

Example 1a Syntheses of other 4'-$R_1$-4-hydroxy substituted Cores useful in synthesis of Subject Compositions Other 4'-$R_1$-4-hydroxy substituted cores are either commercially available or can be synthesized by known methods from readily available starting materials. A variety of achiral tails, i.e., alkyl, alkenyl or alkoxy that are straight chain or branched, or have other variations as described hereinabove, can be appended by known methods to the core 4' relative to the 4-hydroxy substitution on the core. These other 4'-$R_1$-4-hydroxy substituted cores can be used in the methods of the remaining Examples.

Example 2 Syntheses of Chiral 4'-$R_1$-phenyl-4-[(1-methyl-2-halo)alkoxy]benzoates This example illustrates the synthesis of nonracemic chiral 4'-$R_1$-phenyl-4-[(1-methyl-2-halo)alkoxy]benzoates by coupling of 4'-$R_1$-phenyl-4-hydroxybenzoate (X) with a chiral 1-methyl(2,3-epoxy)alkanol, opening the epoxy ring, followed by stereospecific halogenation of the resulting hydroxy group. The procedure is illustrated by the synthesis of 4'-decyloxyphenyl-4[(1S,4-dimethyl-2S-fluoro)pentyloxy]benzoate (XVI, where $R_1$=decyloxy, X=F, and $R_2$=isopropyl) as illustrated in Scheme 4.

Example 2a Synthesis of 4'-decyloxyphenyl-4-[(1S,4-dimethyl-2S-fluoro)pentyloxy]benzoate (MDW 215)

4'-decyloxyphenyl-4-hydroxybenzoate (X, where $R_1$=decyloxy) (2 mmol), (1R,4-dimethyl-2S,3S-epoxy)-pentanol (XIII, where $R_2$=isopropyl) (2 mmol) and triphenyl phosphine (3.0 mmol) were dissolved in dry THF in an argon filled flask. (Synthesis of (1R,4-dimethyl-2S,3S-epoxy)pentanol is described below in Example 2b.) Diisopropyl azodicarboxylate dissolved in dry THF was added dropwise over a period of three hours at 60° C. while stirred with stir bar. The reaction was further stirred overnight at room temperature. The solvent was then rotoevaporated and the residue was subjected to flash chromatography on a silica column using 5% (v/v) ethyl acetate as the eluent to afford the product, 4'-decyloxyphenyl-4-[1S,4-dimethyl-(2S,3S-epoxy)pentyloxy]benzoate (XIV, where $R_1$=decyloxy and $R_2$=isopropyl) in 67% yield.

The product (200 mg) obtained in the above reaction was dissolved in dry $CH_2Cl_2$ in an argon filled flask and cooled to −40° C. Morpholine borane complex (53 mg) and $BF_3$-$Et_2O$ (0.1 ml) were added and stirred for four hours (until the disappearance of the starting material). The reaction was then quenched with water and stirred for one hour at room temperature. Water (50 ml) was added and organic layer was separated. The water layer was extracted twice with $CH_2Cl_2$. The organic layer was washed with brine, dried with anhydrous $MgSO_4$, filtered and rotary evaporated. The residue was flash chromatographed on a silica column 20% (v/v) ethyl acetate in hexanes as the eluent to afford 4'-n-decyloxyphenyl-4-[(1S,4-dimethyl-2R-hydroxy)pentyloxy]benzoate (XV, where $R_1$=decyloxy and $R_2$=isopropyl) in 80% yield.

4'-decyloxyphenyl-4-[1S,4-dimethyl-2R-hydroxy)pentyloxy]benzoate (120 mg) was dissolved in dry $CH_2Cl_2$ in a flame dried, argon filled flask and cooled to −70° C. 0.15 ml of dimethylaminosulfurtrifluoride was added to the cold solution. The reaction was stirred at −70° C. for four hours with a stir bar, then further warmed to room temperature while stirring over a period of eighteen hours. It was then quenched with cold $NaHCO_3$ solution and stirred for 15 minutes. The product was extracted in $CH_2Cl_2$ (two 50 ml portions). Organic layers were combined and washed repeatedly with $NaHCO_3$ solution and brine, dried with anhydrous $MgSO_4$, filtered and rotary evaporated. The residue was flash chromatographed on a silica column using 5% (v/v) ethyl acetate in hexanes to obtain the 30% yield of the 4'-decyloxyphenyl-4-[(1S,4-dimethyl-2S-fluoro)pentyloxy]benzoate (XVI, where $R_1$=decyloxy, X=F and $R_2$=isopropyl). The final product was further purified by crystallization from hexanes at −20° C.

Example 2b Synthesis of 1R,4-dimethyl-(2S,3S-epoxy)-pentanol

The synthesis of 1R,4-dimethyl-(2S,3S-epoxy)-pentanol (XIII, where $R_2$=isopropyl) is illustrated in Scheme 3. The epoxy alcohol, 1S,4-dimethyl-(2S,3S-epoxy)pentanol (XI, where $R_2$=isopropyl) (7.7 mmol), acetic acid (8 mmol) and triphenylphosphine (16 mmol) were dissolved in dry THF and a solution of diisopropyl azodicarboxylate (16 mmol) in dry THF was added dropwise over a period of three hours while stirred with magnetic stir bar. The reaction mixture was stirred overnight. The solvent was rotoevaporated and the residue was subjected to flash chromatography on a silica column using 4% (v/v) ethyl acetate in hexanes as eluent. The spot at $R_f$ 0.46 was collected in 50% yield. TLC resulted in two spots, $R_f$ 0.54 and 0.46. The second spot at $R_f$+0.46 is the major product, the epoxy acetate of XII, where $R_2$=isopropyl. Since both spots are very close it is hard to completely separate the two diastereomers in a single flash chromatography procedure, although the overall yield of the epoxy acetate was high (86%).

The inverted acetate (200 mg) was dissolved in methanol (2 ml). Anhydrous $K_2CO_3$ (50 mg) was added and stirred with a stir bar at room temperature for half an hour. The completion of the reaction was judged by TLC. The solvent was carefully rotoevaporated and the residue was partitioned between ether and water fractions. The water layer was extracted twice with ether. Ether layers were combined, washed with diluted brine, dried over anhydrous $MgSO_4$, filtered and rotoevaporated to obtain the (1R,4-dimethyl-2S,3S-epoxy)-pentanol (XIII, where $R_2$=isopropyl).

Example 2c Synthesis of 4'-decyloxyphenyl-4-[(1R,4-dimethyl-2R-fluoro)pentyloxy]benzoate To synthesize 4'-decyloxyphenyl-4-[(1R,4-dimethyl-2R-fluoro)pentyloxy]benzoate, the enantiomer of 4'-decyloxyphenyl-4-[(1S,4-dimethyl-2S-fluoro)pentyloxy]benzoate (Example 2a), the method of Example 2a is followed with the exception that (1S,4-dimethyl-2R,3R-epoxy)pentanol, the enantiomer of (1R,4-dimethyl-2S,3S-epoxy)pentanol (XIII, where $R_2$=isopropyl, used in Example 2a) is used in place of (1R,4-dimethyl-2S,3S-epoxy)pentanol. (1S,4-dimethyl-2R,3R-epoxy)pentanol is commericially available or can be synthesized by known methods from readily available starting materials.

Example 2d Synthesis of 4'-decyloxyphenyl-4-[(1R,4-dimethyl-2S-fluoro)pentyloxy]benzoate To synthesize 4'-decyloxyphenyl-4-[(1R,4-dimethyl-2S-fluoro)pentyloxy]benzoate, the diastereomer of 4'-decyloxyphenyl-4-[(1S,4-dimethyl-2S-fluoro)pentyloxy]benzoate (Example 2a), the method of Example 2a is followed with the exception that (1S,4-dimethyl-2S,3S-epoxy)pentanol (XI, where $R_2$=isopropyl), a diastereomer of (1R,4-dimethyl-2S,3S-epoxy)pentanol (XIII, where $R_2$=isopropyl), is used in place of (1R,4-dimethyl-2S,3S-epoxy)pentanol. (1S,4-dimethyl-2S,3S-epoxy)pentanol or other compounds of formula XI can be synthesized by known methods from readily available starting materials.

Example 3 Synthesis of 4'-$R_1$-phenyl-4-[(1-methyl-2,3-dihalo)alkoxy]benzoates To synthesize 4'-$R_1$-phenyl-4-[(1-methyl-2,3-dihalo)alkoxy]benzoates, 4'-$R_1$-phenyl-4-hydroxybenzoate (X) is coupled to a chiral 1-methyl-2-epoxy alkanol, the epoxy ring is opened and treated with a halogenating agent. The synthesis of 4'-$R_1$-phenyl-4-[(1-methyl-2,3-dihalo)alkoxy]-benzoates is exemplified by the synthesis of 4'-decyloxyphenyl-4-[(1S,4-dimethyl-2R,3R-difluoro)pentanyloxy]benzoate (XIX, where $R_1$=decyloxy, X and y=F and $R_2$=isopropyl) as illustrated in Scheme 5.

Example 3a Synthesis of 4'-decyloxyphenyl-[1S,4-dimethyl-2R,3R-difluoro)pentanyloxy]benzoate (MDW194)

4'-decyloxyphenyl-4-hydroxybenzoate (X, where $R_1$=decyloxy) (0.77 mmol), (1R,4-dimethyl-2S,3S epoxy)pentanol (XIII, where $R_2$=isopropyl) (0.8 mmol) and triphenylphosphine (1.5 mmol) were dissolved in 10 ml of dry THF. A solution of diisopropylazo- dicarboxylate (3 mmol) in 1 ml of dry THF was added dropwise over a period of two hours while stirred with a stir bar. The solvent was then taken off under vacuum and the residue was flash chromatographed on a silica column using 5% (v/v) ethyl acetate in hexanes as eluent to afford the 4'-decyloxyphenyl-4-[(1S,4-dimethyl-2S,3S-epoxy)pentanyloxy]benzoate (XVII, where $R_1$=decyloxy and $R_2$=isopropyl) in 84% yield.

240 mg (0.52 mmol) of the 4'-decyloxyphenyl-4-[(1S,4-dimethyl-2S,3S-epoxy)pentanyloxy]benzoate was dissolved in 10 ml of dry $CH_2Cl_2$ and cooled to 0° C. 0.5 ml of HF in pyridine was added to the cold solution and stirred for one hour with a stir bar. The reaction was judged complete by TLC. It was then quenched with cold water and stirred further for 15 minutes. The solvent was rotary evaporated and the residue was flash chromatographed on a silica column using 10% (v/v) ethyl acetate in hexanes to obtain 84% of the fluorohydrin product (XVIII, where $R_1$=decyloxy, X=F and $R_2$=isopropyl).

In a flame dried argon-filled flask, the fluorohydrin product (280 mg) from the above reaction was dissolved in 20 ml of dry $CH_2Cl_2$ and cooled to −70° C. 0.1 ml of dimethyl aminosulfurtrifluoride (DAST) was added to the reaction mixture and was allowed to stir for two hours at −70° C. The reaction mixture was stored in the refrigerator overnight. It was quenched with cold $NaHCO_3$ solution and stirred for 15 minutes. The product was extracted in $CHCl_2$ (two 50 ml portions). Organic layers were combined and washed repeatedly with $NaHCO_3$ solution and brine, dried with anhydrous $MgSO_4$, filtered and rotary evaporated. The residue was flash chromatographed on a silica column using 5% (v/v) ethyl acetate in hexanes to obtain 40% yield. The final product, 4'-decyloxyphenyl-4-[(1S,4-dimethyl-2R,3R-difluoro)pentanyloxy]-benzoate (XIX, where $R_1$=decyloxy, X and Y=F and $R_2$=isopropyl) was further purified by crystallization from hexanes.

Example 3b Synthesis of 4'-decyloxyphenyl-4-[(1R,4-dimethyl-2S,3S-difluoro)pentanyloxy]-benzoate The synthesis of 4'-decyloxyphenyl-4-[(1R,4-dimethyl-2S,3S-difluoro)pentanyloxy]-benzoate, the enantiomer of 4'-decyloxyphenyl-4-[(1S,4-dimethyl-2R,3R-difluoro)pentanyloxy]benzoate (Example 3a), is accomplished by following the method of Example 3a with the exception that (1S,4-dimethyl-2R,3R-epoxy)pentanol, the enantiomer of (1R,4-dimethyl-2S,3S epoxy)-pentanol (XIII, where $R_2$=isopropyl), is used in place of (1R,4-dimethyl-2S,3S epoxy)pentanol.

Example 3c Synthesis of 4'-decyloxyphenyl-4-[(1R,4-dimethyl-2R,3R-difluoro)pentanyloxy]-benzoate To synthesize 4'-decyloxyphenyl-4-[(1R,4-dimethyl-2R,3R-difluoro)pentanyloxy]benzoate, a diastereomer of 4'-decyloxyphenyl-4-[(1S,4-dimethyl-2R,3R-difluoro)pentanyloxy]benzoate (Example 3a), the method of Example 3a is followed with the exception that (1S,4-dimethyl-2S,3S-epoxy)pentanol (XI, where $R_2$=isopropyl), a diastereomer of (1R,4-dimethyl-2S,3S-epoxy)pentanol (XIII, where $R_2$=isopropyl), is used in place of (1R,4-dimethyl-2S,3S epoxy)pentanol.

This invention has been described and illustrated by reference to several preferred embodiments, but it is not intended to limit the invention by doing so. It is intended that the invention encompass all enantiomers and regioisomers of the general formula:

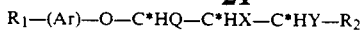

It is also intended that the invention include mixtures of two or more compositions of the subject invention, and FLC formulations in which these compounds are admixed with each other or with other compounds including LC and FLC materials.

What is claimed is:

1. A chiral nonracemic compound of the general formula:

wherein:
- $R_1$ is an achiral tail having two to sixteen carbons and is selected from the group consisting of alkyl, alkyl sulfide, alkyl ether, alkoxy, alkoxy sulfide, alkoxy ether, alkenyl, alkenyl sulfide, and alkenyl ether,
- Ar is selected from the group consisting of phenylbenzoates, phenylpyrimidines, biphenyls, phenylpyridines, biphenylbenzoates, diphenylpyrimidines, diphenylpyridines, terphenyls, phenyldiazines, diphenyldiazenes, and diphenylthiadiazoles,
- * denotes a chiral or potentially chiral carbon,
- X is a halide and Y is H or a halide,
- $R_2$ comprises the distal segment of the chiral tail and is an alkyl or alkenyl group having one to ten carbon atoms, and
- the —O—C*H(CH$_3$)—C*HX—C*HY— segment comprises the chiral proximal segment of the chiral tail, and the proximal segment is selected from the diastereomers and enantiomers:

| | |
|---|---|
| 1S-methyl-2S-halo | 1R-methyl-2R-halo |
| 1S-methyl-2R-halo | 1R-methyl-2S-halo |
| 1R-methyl-2R,3R-dihalo | 1S-methyl-2S,3S-dihalo |
| 1R-methyl-2R,3S-dihalo | 1S-methyl-2S,3R-dihalo |
| 1R-methyl-2S,3S-dihalo | 1S-methyl-2R,3R-dihalo |
| 1R-methyl-2S,3R-dihalo | 1S-methyl-2R,3S-dihalo. |

2. The compound of claim 1, wherein $R_1$ comprises five to sixteen carbons.

3. The compound of claim 2, wherein $R_1$ comprises eight carbons.

4. The compound of claim 1, wherein $R_1$ is selected from the group of straight-chain and branched.

5. The compound of claim 1, wherein $R_2$ consists of 3 carbons.

6. The compound of claim 1, wherein $R_2$ is selected from the group of straight chain and branched.

7. The compound of claim 1, wherein X and Y are independently selected from the group of chloride and fluoride.

8. The compound of claim 1, selected from the group consisting of 4'-decyloxyphenyl-4-[(1S,4-dimethyl-2S-fluoro)pentyloxy]benzoate, 4'-decyloxyphenyl-4-[(1R,4-dimethyl-2R-fluoro)pentyloxy] benzoate. 4'-decyloxyphenyl-[1S,4-dimethyl-2R,3R-difluoro)pentyloxy]benzoate, and 4'-decyloxyphenyl4-[(1R, 4-dimethyl-2S,3S-difluoro)pentyloxy]-benzoate.

9. A ferroelectric liquid crystal composition comprising the compound of claim 1.

10. The compound of claim 1, wherein X is fluoride and Y is H or a fluoride.

11. The compound of claim 1 wherein Y is H and the chiral proximal segment is selected from the group consisting of:

| | |
|---|---|
| 1S-methyl-2S-halo | 1R-methyl-2R-halo |
| 1S-methyl-2R-halo | 1R-methyl-2S-halo. |

12. The compound of claim 11 wherein $R_1$ comprises five to sixteen carbons.

13. The compound of clam 11, wherein X is selected from the group of chloride and fluoride.

14. The compound of claim 11, wherein X is a fluoride.

15. A ferroelectric liquid crystal composition comprising the compound of claim 11.

* * * * *

UNITED STATES PATENT AND TRADEMARK OFFICE
CERTIFICATE OF CORRECTION

PATENT NO. : 5,167,855
DATED : Dec. 1, 1992
INVENTOR(S) : Michael Wand; Rohini Vohra; David Walba It is certified that error appears in the above-identified patent and that said Letters Patent is hereby corrected as shown below:

Title page, Item [54], second line of title, please insert --CONTAINING-- between "COMPOSITIONS" AND "CHIRAL".

At Col. 1, Item [57], bridging lines 9-10 of the text, please rewrite "-O-C*H(CH$_3$)-C*HY-C*HY-CH$_2$-O-" as -- -O-C*H(CH$_3$)-C*HX-C*HY-CH$_2$- --. At column 3, line 21, please rewrite "pyridine-3-carboxylicacidesters" as --pyridine-3-carboxylic acid esters--. At column 3, line 28, please rewrite "(trans-4-ethyl-cyclohexyl)- 5-nicotinic acid3-fluoro-4-" as --(trans-4-ethyl-cyclohexyl)-5-nicotinic acid 3-fluoro-4- --. At column 5, bridging lines 34-35, please rewrite "biphenyl pyridines," as --biphenylpyridines,--. At column 6, line 16, please rewrite "phenylpridines." as --phenylpyridines.--. At column 10, line 42, please rewrite "(1R,4-dimethyl-2S,3S epoxypentanol" as --(1R,4-dimethyl-2S,3S-epoxypentanol--. At column 10, line 44, please rewrite "2S,3S epoxypentanol." as --2S,3S-epoxypentanol.--. At column 12, in Scheme 3, please rewrite the structure of Compound XI as --
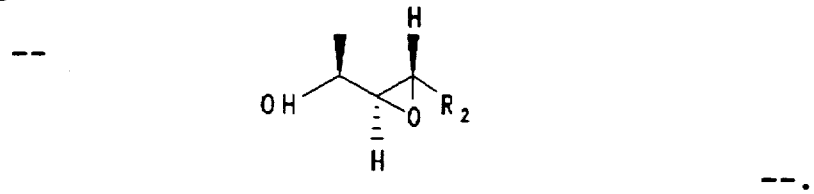
--.

At column 12, in Scheme 3, please rewrite the structure of Compound XII as

--
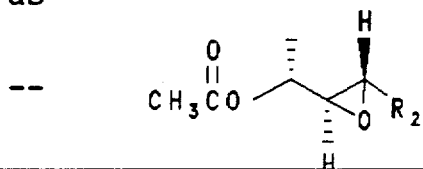

UNITED STATES PATENT AND TRADEMARK OFFICE
CERTIFICATE OF CORRECTION

PATENT NO. : 5,167,855
DATED : Dec. 1, 1992
INVENTOR(S) : Michael Wand; Rohini Vohra; David Walba It is certified that error appears in the above-identified patent and that said Letters Patent is hereby corrected as shown below:

At column 11, in Scheme 4, at column 12, in Scheme 3, and at column 13, in Scheme 5, all three occurrences, please rewrite the structure of Compound XIII as

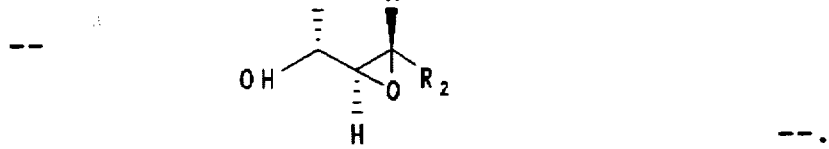

At column 12, in Scheme 4, please rewrite the structure of Compound XIV as

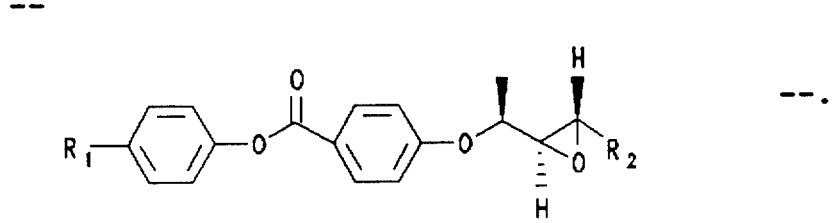

At column 13, line 67, please rewrite "also-be" as --also be--.
At column 14, in Scheme 5, please rewrite the structure of Compound XVII as

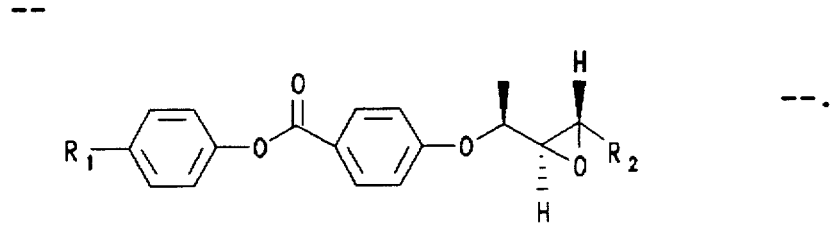

UNITED STATES PATENT AND TRADEMARK OFFICE
CERTIFICATE OF CORRECTION

PATENT NO. : 5,167,855
DATED : Dec. 1, 1992
INVENTOR(S) : Michael Wand; Rohini Vohra; David Walba It is certified that error appears in the above-identified patent and that said Letters Patent is hereby corrected as shown below:

At column 17, line 21, please rewrite "decycloxyphenyl-4-methoxyoxycarbonyloxybenzoate" as --decycloxyphenyl-4-methoxycarbonyloxybenzoate--. At column 22, line 35, please rewrite "clam" as --claim--.

Signed and Sealed this

Twenty-second Day of February, 1994

*Attest:*

BRUCE LEHMAN

*Attesting Officer*    Commissioner of Patents and Trademarks